US005981471A

United States Patent [19]

Papathanassiu et al.

[11] Patent Number: 5,981,471
[45] Date of Patent: Nov. 9, 1999

[54] COMPOSITIONS AND METHODS FOR INHIBITING CELLULAR PROLIFERATION

[75] Inventors: Adonia E. Papathanassiu, Silver Spring, Md.; Shawn J. Green, Vienna, Va.

[73] Assignee: EntreMed, Inc., Rockville, Md.

[21] Appl. No.: 08/796,850

[22] Filed: Feb. 6, 1997

[51] Int. Cl.⁶ .......................... A61K 38/55; A61K 38/06
[52] U.S. Cl. .................................................................. 514/2
[58] Field of Search .................................................. 514/2

[56] References Cited

U.S. PATENT DOCUMENTS

| | | | |
|---|---|---|---|
| 4,552,888 | 11/1985 | Koppel et al. | 514/174 |
| 4,994,443 | 2/1991 | Folkman et al. | 514/56 |
| 5,001,116 | 3/1991 | Folkman et al. | 514/171 |
| 5,021,404 | 6/1991 | Folkman et al. | 514/26 |
| 5,358,959 | 10/1994 | Halperin et al. | 514/296 |
| 5,653,744 | 8/1997 | Khouri | 623/1 |

FOREIGN PATENT DOCUMENTS

| | | |
|---|---|---|
| WO97/3560 | 2/1997 | WIPO . |
| 97/09063 | 3/1997 | WIPO . |

OTHER PUBLICATIONS

Cardiff, R.D., "Protoneoplasia: The Molecular Biology of Murine Mammary Hyperplasia", *Advances in Cancer Research*, vol. 42, pp. 167–190 (1984) [Abstract Only].
Davies, et al., "Pathobiology of Intimal Hyperplasia", *British Journal of Surgery*, vol. 81, pp. 1254–1269 (1994) [Abstract Only].
Haas, A. F. et al., "Angiolymphoid Hyperplasia with Eosinophilia of the Hand", *Journal of Dermatologic Surgery and Oncology*, vol. 17, pp. 731–734 (1991) [Abstract Only].
Kamikubo, Y. et al., "Human Recombinant Tissue–Factor Pathway Inhibitor Prevents the Proliferation of Cultured Human Neonatal Aortic Smooth Muscle Cells", FEBS Letters, vol. 407, pp. 116–120 (1997).
Khouri, R. K. et al., "Local Application of Tissue Factor Pathway Inhibitor (TFPI) Inhibits Intimal Hyperplasia Induced by Arterial Interventions", *Surgical Forum*, vol. 46, pp. 389–391 (1995).
Steinhubl, S.R. et al., "Local Delivery of Tissue Factor Pathway Inhibitor (TFPI) to Reduce Neointimal Proliferation in the Porcine Coronary Balloon Injury Model", *Journal of the American College of Cardiology*, vol. 29, No. 2, Supp. (A), pp. 97557–97557, Abstract No. 975–57.
Dinbergs et al. Journal of Biological Chemistry, 271 (47) 29822–9, Dec. 1996.
Koyama et al. American Journal of Pathology, 148 (3) 749–61, Mar. 1996.
Ishino et al. Folia Psychiat.Neurol.Jap., 27/3 (207–221), Jan. 1973.
Steinhubl S. et al. Local delivery of tissue factor pathway inhibitor (TFP) to reduce neonintimal proliferation . . . 46th Annual Scientific Session of the American College of Cardiology, Anaheim, California, USA, Mar. 16–19, 1997. Journal of the America, Jan. 1997.

Haas et al. Journal of Dermatologic Surgery and Oncology, 17 (9) 731–4, Sep. 1991.
Srigley, J.R. Seminars in Diagnostic Pathology,) 5(3) 254–72, Sep. 1988.
Cardiff, A.D. Advances in Cancer Research, 42, 167–90, Jan. 1984.
Ferenczy, A. Annales de Pathologie, 3 (3) 189–201, Sep. 1983.
Khouri et al. Surgical Forum 46, 389–391, Mar. 1995.
Algire, G.H. et al., "Vascular reactions of normal and malignant tumors in vivo. I. Vascular reactions of mice to wounds and to normal and neoplastic transplants", *J. Natl. Canc. Inst.*, vol. 6, pp. 73–85 (1945).
Bok, Robert A. et al., "Quantitative Characterization of the Binding of Plasminogen to Intact Fibrin Clots, Lysine–Sepharose, and Fibrin Cleaved by Plasmin", *American Chemical Society*, pp. 3279–3286, (1985).
Brem, H. et al., "Interstitial chemotherapy with drug polymer implants for the treatment of recurrent gliomas", *J. Neurosurg.*, vol. 74, pp. 441–446 (1991).
Broze, George J. Jr., M.D., "Tissue Factor Pathway Inhibitor and the Revised Theory of Coagulation" *Annu. Rev. Med.*, vol. 46, pp. 103–112 (1995).
Cao, Y. et al., "gro–β, α –C–X–C–Chemokine, Is an Angiogenesis Inhibitor That Suppresses the Growth of Lewis Lung Carcinoma in Mice", *J. Esp. Med.*, vol. 182, pp. 2069–2077 (1995).
Cao, Y. et al., "Kringle Domains of Human Angiostatin", *The Journal of Biological Chemistry*, vol. 271, pp. 1–7 (1996).
Chen, C. et al., "A Strategy to Discover Circulating Angiogenesis Inhibitors Generated by Human Tumors", *Canc Resch.*, vol. 55, pp. 4230–4233 (1995).
Contrino, J., "In situ detection of tissue factor in vascular endothelial cells: Correlation with the malignant phenotype of human breast disease", *Nature Medicine*, vol. 2, No. 2, pp. 209–215, (Feb. 1996).
Crum, et al., "A New Class of Steroids Inhibits Angiogenesis in the Presence of Heparin or a Heparin Fragment", *Science*, vol. 230, pp. 1375–1381, (1985).

(List continued on next page.)

*Primary Examiner*—Cecilia J. Tsang
*Assistant Examiner*—Michael Borin
*Attorney, Agent, or Firm*—Jones & Askew, LLP

[57] ABSTRACT

Compositions and methods for inhibiting cellular proliferation wherein the composition contains Tissue Factor Pathway Inhibitor (TFPI), a TFPI homolog, or an active fragment thereof. TFPI exhibits potent anti-proliferative activity on human and other animal cells, particularly endothelial cells. More particularly, the TFPI, TFPI homolog, and inhibitory fragment thereof may be combined with a pharmaceutically acceptable excipient or carrier and used to inhibit angiogenesis and angiogenesis-related diseases such as cancer, arthritis, macular degeneration, and diabetic retinopathy.

9 Claims, 7 Drawing Sheets

OTHER PUBLICATIONS

Enjyoji, K. et al., "Effect of Heparin on the Inhibition of Factor Xa by Tissue Factor Pathway Inhibitor: A Segment, $Gly^{212}$—$Phe^{243}$, of the third Kunitz Domain Is a Heparin–Binding Site", *Biochemistry*, vol. 34, No. 17, pp. 5725–5735 (1995).

Folkman, J., "Tumor angiogenesis and tissue factor", *Nature Med.*, vol. 2, pp. 167–168 (1996).

Folkman, J., "What is the Evidence that Tumors are Angiogenesis Dependent?", *J. Natl Canc Inst.*, vol. 82, pp. 4–6 (1990).

Folkman, J., "Angiogenesis in cancer, vascular, rheumatoid and other disease", *Nature Medicine*, vol. 1, No. 1, pp. 27–31 (1995).

Folkman, J., "Long–term culture of capillary endothelial cells", *Proc. Natl. Acad. Sci. USA*, vol. 76, pp. 5217–5221 (1979).

Folkman, J. et al., "Induction of angiogenesis during the transition from hyperplasia to neoplasia", *Nature*, vol. 339, pp. 58–61 (1989).

Folkman, J. et al., "Tumor Behavior in Isolated Perfused Organs In Vitro Growth and Metastases of Biopsy Material in Rabbit Thyroid and Canine Intestinal Segment", *Annals of Surgery*, vol. 164, No. 3, pp. 491–501 (1996).

Folkman, J., "Angiogenesis and Its Inhibitors", *Important Advances in Oncology*, J.B. Lippincott Company, pp. 42–62 (1985).

Folkman, J., "Tumor Angiogenesis Therapeutic Implications", *NE J. of Med.*, No. 18, pp. 1182–1186 (1971).

Gimbrone, M.A. et al., "Tumor Growth and Neovascularization An Experimental Model using the Rabbit Cornea", *J. Natl. Canc. Inst.*, vol. 52, No. 2, pp. 413–427 (1974).

Gimbrone, M.A. et al., "Tumor Dormancy in Vivo by Prevention of Neovascularization", *J. of Experi. Med.*, vol. 136, pp. 261–276 (1972).

Good, D.J. et al., "A tumor suppressor–dependent inhibitor of angiogenesis is immunologically and functionally indistinguishable from a fragment of thrombospondin", *Proc. Nat. Acad. Sci. USA*, vol. 87, pp. 6624–6628 (1990).

Gross, J.L. et al., "Modulation of Solid Tumor Growth in vivo by bFGF", *Proc. Amer. Assoc. Canc. Resch*, vol. 31, p. 79 (1990).

Gupta, S.K. et al., "A potent inhibitor of endothelial cell proliferation is generated by proteolytic cleavage of the chemokine platelet factor 4", *Proc. Natl. Acad. Sci. USA*, vol. 92, pp. 7779–7803 (1995).

Holmgren, L. et al., "Dormancy of micrometastases Balanced proliferation and apoptosis in the presence of angiogenesis suppression", *Nature Medicine*, vol. 1, No. 2, pp. 149–153 (1995).

Homandberg, G.A. et al., "Heparin–binding fragments of fibronectin are potent inhibitors of endothelial cell growth", *Am. J. Path.*, vol. 120, pp. 327–332 (1985).

Ingber, D. et al., "Synthetic analogues of fumagillin that inhibit angiogenesis and suppress tumor growth", *Nature*, vol. 348, pp. 555–557 (1990).

Kim, K. J. et al., "Inhibition of vascular endothelial growth factor–induced angiogenesis suppresses tumor growth in vivo", *Nature*, vol. 362, pp. 841–844 (1993).

Knighton, D. et al., "Avascular and Vascular Phases of Tumor Growth in the Chick Embryo", *Br. J. Cancer*, vol. 35, pp. 347–356 (1977).

Lindahl, A., "Coagulation Inhibition and Activation in Pancreatic Cancer", *Cancer*, vol. 70, No. 8, pp. 2067–2072.

Lupu, C. et al., "Thrombin Induces the Redistribution and Acute Release of Tissue Factor Pathway Inhibitor from Specific Granules Within Human Endothelial Cells in Culture", *Arteriosclerosis, Thrombosis, and Vascular Biology*, vol. 15, No. 11, pp. 2055–2062 (Nov. 1995).

Maione, T.E. et al., "Inhibition of Angiogenesis by Recombinant Human Platelet Factor–4 and Related Peptides", *Science*, vol. 247, pp. 77–79 (1990).

McGee, M. et al., "Simultaneous Expression of Tissue Factor and Tissue Factor Pathway Inhibitor by Human Monocytes. A Potential Mechanism for Localized Control of Blood Coagulation", *J. Exp. Med.*, vol. 179, pp. 1847–1854 (Jun. 1994).

Miyagi, Y. et al., "cDNA Cloning and mRNA Expression of a Serine Proteinase Inhibitor Secreted by Cancer Cells: Identification as Placenta Protein 5 and Tissue Factor Pathway Inhibitor–2", *J. Biochem*, vol. 116, pp. 939–942 (1994).

Narita, Masaaki et al., "Two Receptor Systems are Involved in the Plasma Clearance of Tissue Factor Pathway Inhibitor in Vivo", *J. of Bio. Chem.*, vol. 270, No. 42, pp. 24800–24804 (1995).

Nguyen, M. et al., "Quantitation of Angiogenesis and Antiangiogenesis in the Chick Embryo Chorioallantoic Membrane", *Microvascular Research*, vol. 47, pp. 31–49 (1994).

Nguyen, M. et al., "Elevated Levels of the Angiogenic Peptide Basic Fibroblast Growth Factor in Urine of Bladder Cancer Patients", *J. of Nat. Canc. Inst.*, vol. 85, No. 3, pp. 241–242 (1993).

Novotny, W.F. et al., "Purification and Characterization of the Lipoprotein–Associated Coagulation Inhibitor from Human Plasma", *J. Biol. Chem.*, vol. 264, pp. 18832–18837 (1989).

O'Reilly et al., "Endogenous Inhibitors of Angiogenesis", *Proc. Am. Assoc. Canc. Resch.*, vol. 37, p. 669 (1996).

O'Reilly et al., "Angiostatin induces and sustains dormancy of human primary tumors in mice", *Nature Medicine*, vol. 2, No. 6, pp. 689–692 (1996).

O'Reilly et al., "The suppression of Tumor Metastases by a Primary Tumor", *Surgical Forum*, vol. XLIV, pp. 474–476 (1993).

O'Reilly et al., "Angiostatin A Novel Angiogenesis Inhibitor that Mediates the Suppression of Metastases by a Lewis Lung Carcinoma", *Cell*, vol. 79, pp. 315–328 (1994).

O'Reilly et al., "Angiostatin: A Circulating Endothelial Cell Inhibitor That Suppresses Angiogenesis and Tumor Growth", *Cold Spring Harbor Symposia on Quantitative Biology*, vol. LIX, pp. 471–482 (1994).

Obeso, J. et al., "Methods in Laboratory Investigation/A Hemangioendothelioma–Derived Cell Line Its Use as a Model for the Study of Endothelial Cell Biology", *Laboratory Investigation*, vol. 63, No. 2, p. 159 (1990).

Osterud, B. et al., "Sites of Tissue Factor Pathway Inhibitor (TFPI) and Tissue Factor Expression under Physiologic and Pathologic Conditions", *Thrombosis and Haemostasis*, vol. 73, pp. 873–875 (1995).

Parangi, S. et al., "Antiangiogenic therapy of transgenic mice impairs de novo tumor growth", *Proc. Natl. Acad. Sci. USA*, vol. 93, pp. 2002–2007 (1996).

Passaniti, A. et al., "Methods in Laboratory Investigation/A Simple, Quantitative Method for Assessing Angiogenesis and Antiangiogenic Agents Using Reconstituted Basement Membrane, Heparin and Fibroblast Growth Factor", *Lab. Invest.*, vol. 67, No. 4, pp. 519–528 (1992).

Petesen, L. C. et al., "Inhibitory Properties of a Novel Human Kunitz–Type Protease Inhibitor Homologous to Tissue Factor Pathway Inhibitor", *Biochemistry*, vol. 35, pp. 266–272 (1996).

Rastinejad, F. et al., "Regulation of the activity of a new inhibitor of angiogenesis by a cancer suppressor gene", *Cell*, vol. 56, pp. 345–355 (1989).

Samanma, M.M. et al., "Mechanisms for the Antithrombotic Activity in Man of Low Molecular Weight Heparins (LMWHs)", *Haemostasis*, vol. 24, pp. 105–117 (1994).

Sprecher, C. A. et al., "Molecular cloning, expression, and partial characterization of a second human tissue–factor–pathway inhibitor", *Pro. Natl. Acad. Sci. USA*, vol. 91, pp. 3353–3357 (1994).

Srivastava, A. et al., "The Prognostic Significance of Tumor-ascularity in Intermediate–Thickness (0.76–4.0mm Thick) Skin Melanoma", *Am. J. of Path.* vol. 133, No. 2, pp. 419–424 (1988).

Taylor, S. et al., "Protamine is an inhibitor of angiogenesis", *Nature*, vol. 297, pp. 307–312, (1982).

Teicher, B. A. et al., "Potentiation of cytotoxic cancer therapies by TNP–470 alone and with other antiangiogenic agents", *Int. J. Canc.*, vol. 57, pp. 1–6 (1994).

Voest, E. E. et al., "Inhibition of Angiogenesis in Vivo by Interleukin 12", *J. Natl. Can. Inst.*, vol. 87, pp. 581–586 (1995).

Warshawsky, I. et al., "The Carboxy Terminus of Tissue Factor Pathway Inhibitor is Required for Interacting with Hepatoma Cells in Vitro and In Vivo", *The American Society for Clinical Investigation, Inc.*, vol. 95, pp. 1773–1781 (1995).

Warshawsky, I. et al., "The low density lipoprotein receptor–related protein mediates the cellular degradation of tissue factor pathway inhibitor", *Proc. Natl. Adad. Sci. USA*, vol. 91, pp. 6664–6668, (1994).

Weidner, N. et al., "Tumor Angiogenesis: A New Significant and Independent Prognostic Indicator in Early–Stage Breast Carcinoma", *J. Natl. Canc. Inst.*, vol. 84, pp. 1875–1887 (1992).

Weidner, N. et al., "Tumor Angiogenesis Correlates with Metastasis in Invasive Prostate Carcinoma", *Am. J. Path.*, vol. 143, No. 2, pp. 401–409 (1993).

Weidner, N. et al., "Tumor Angiogenesis and Metastasis—Correlation in Invasive Breast Carcinoma", *NE J. of Med.*, vol. 324, No. 1, pp. 1–8 (1991).

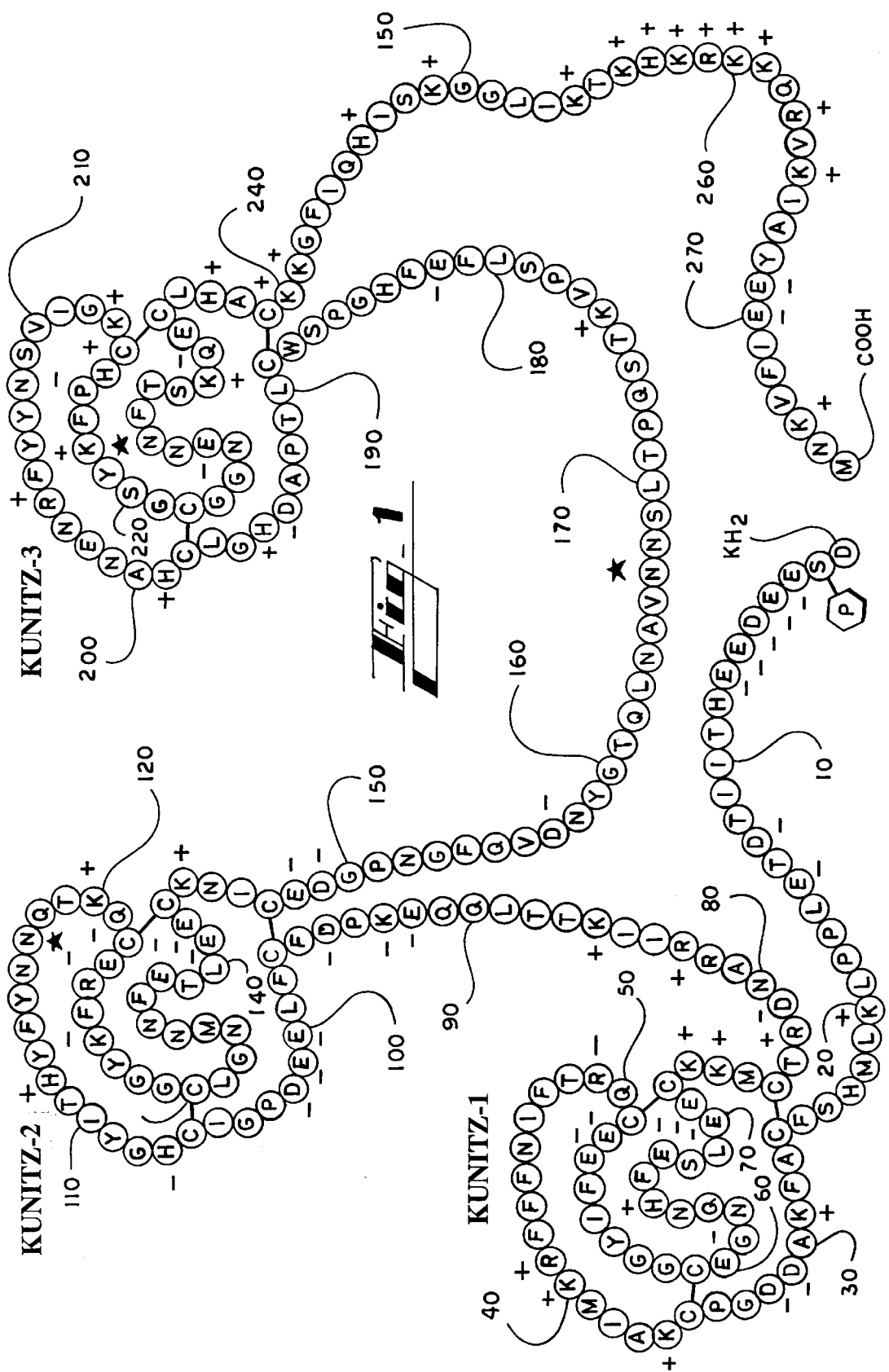

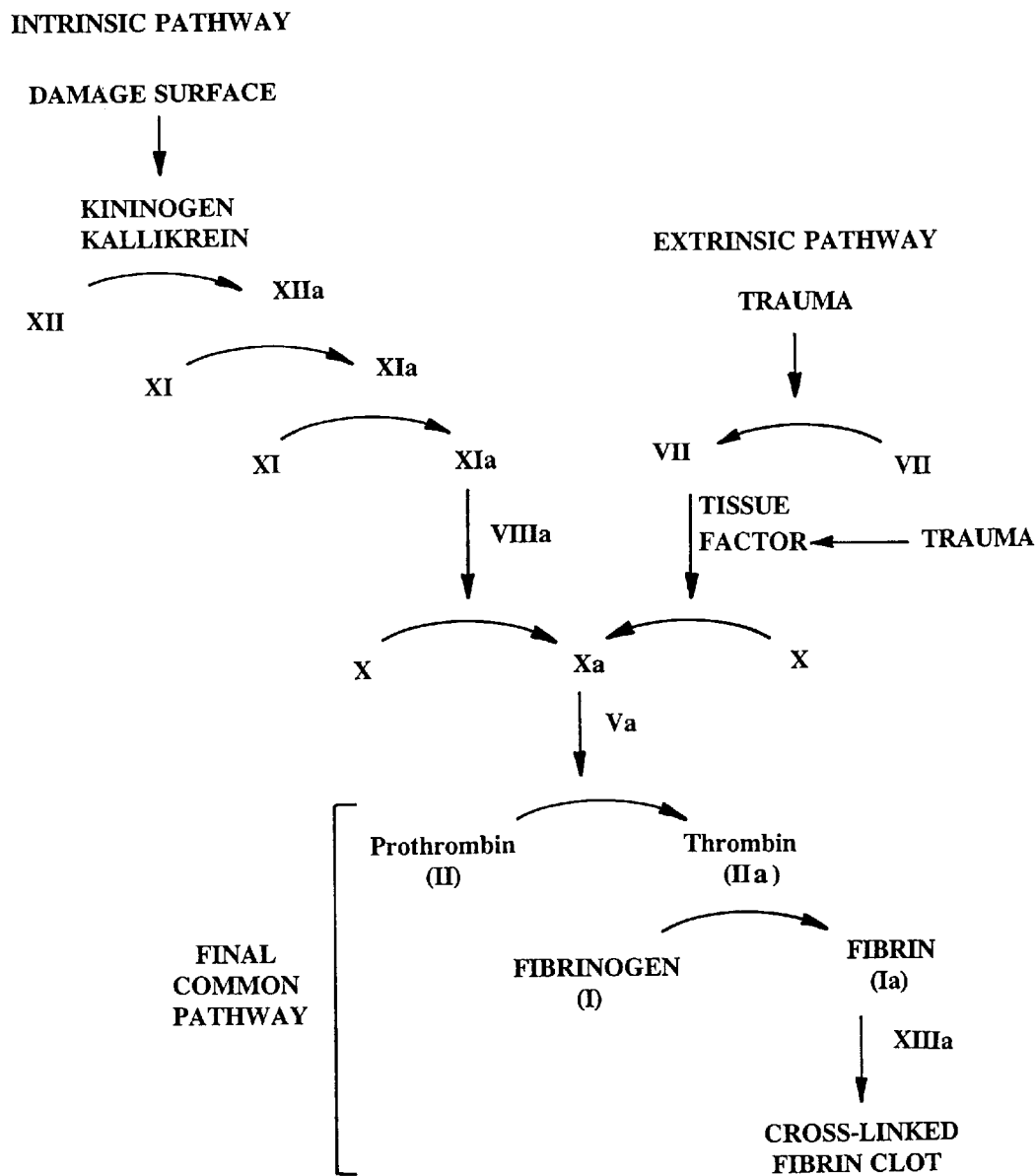
Fig_2
PRIOR ART

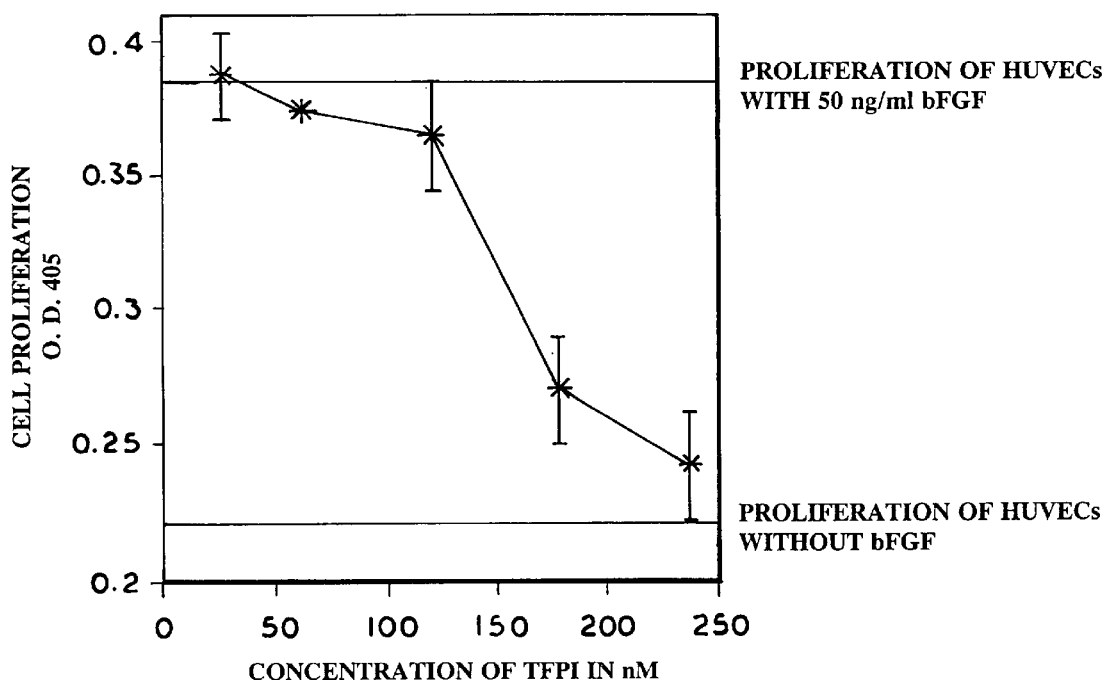
Fig_3C
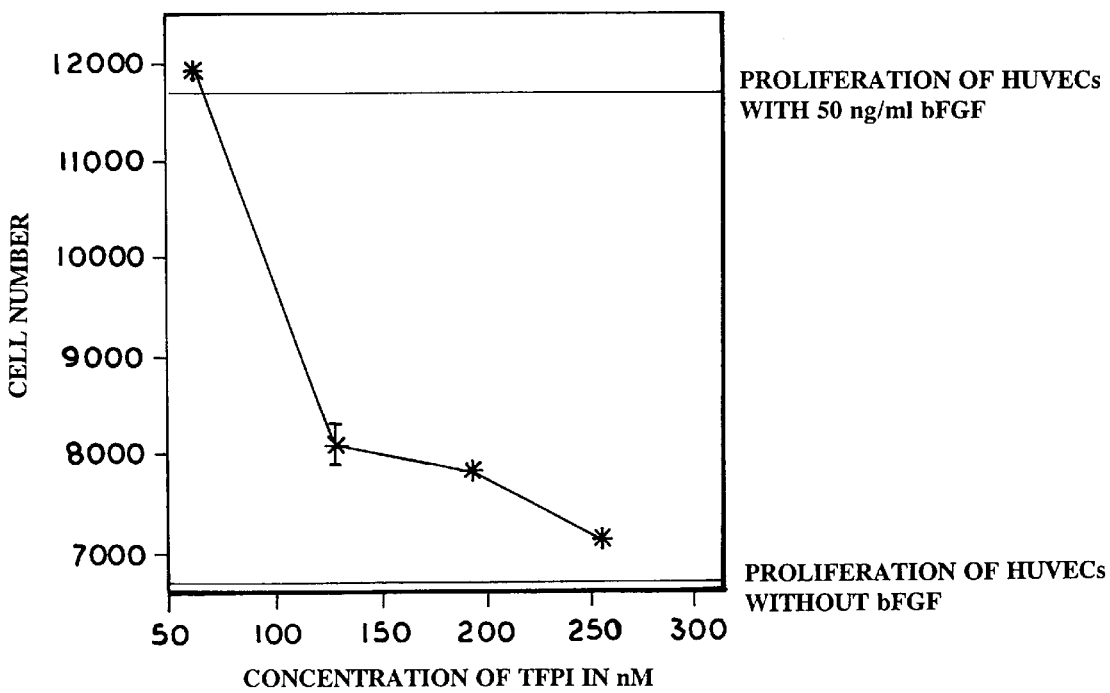
Fig_3D

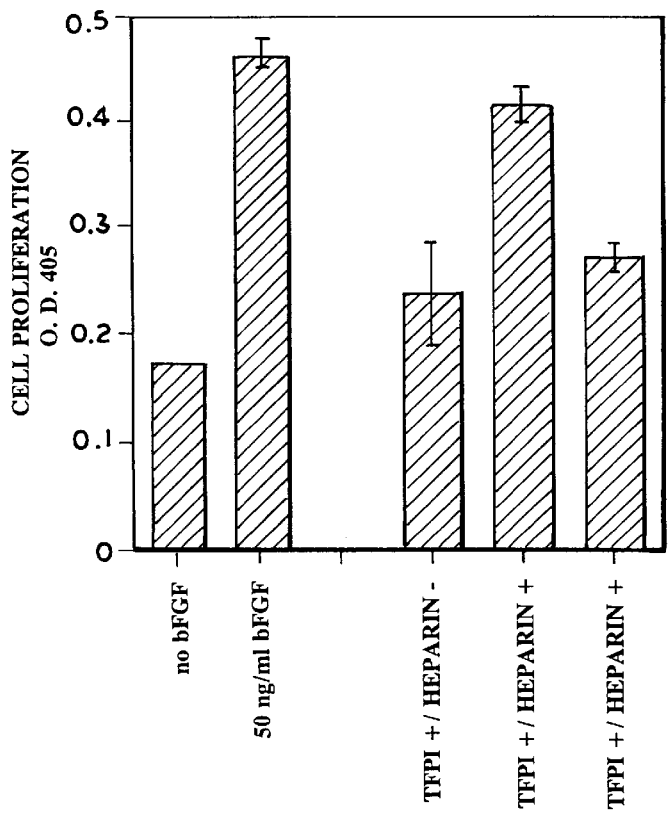
Fig_5A
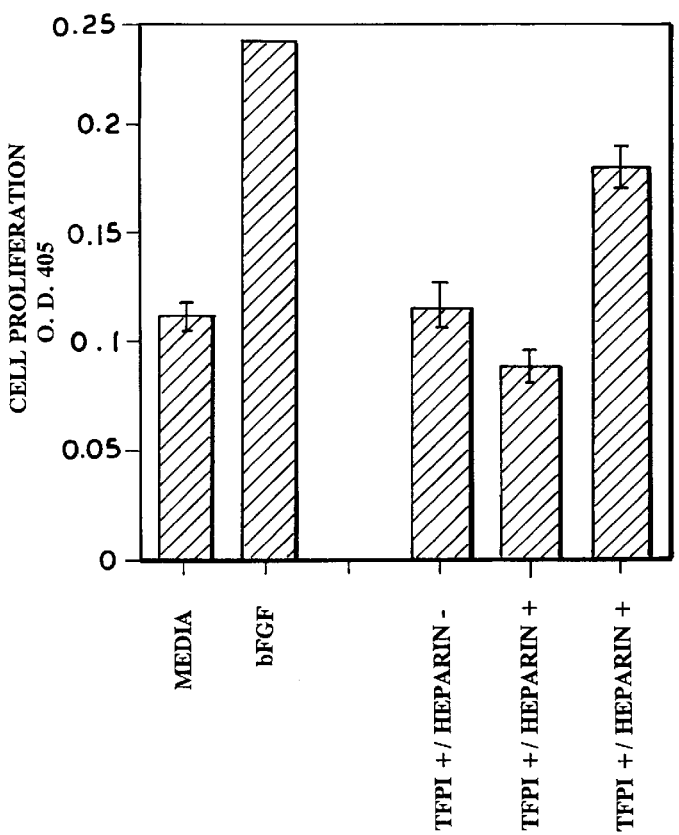
Fig_5B

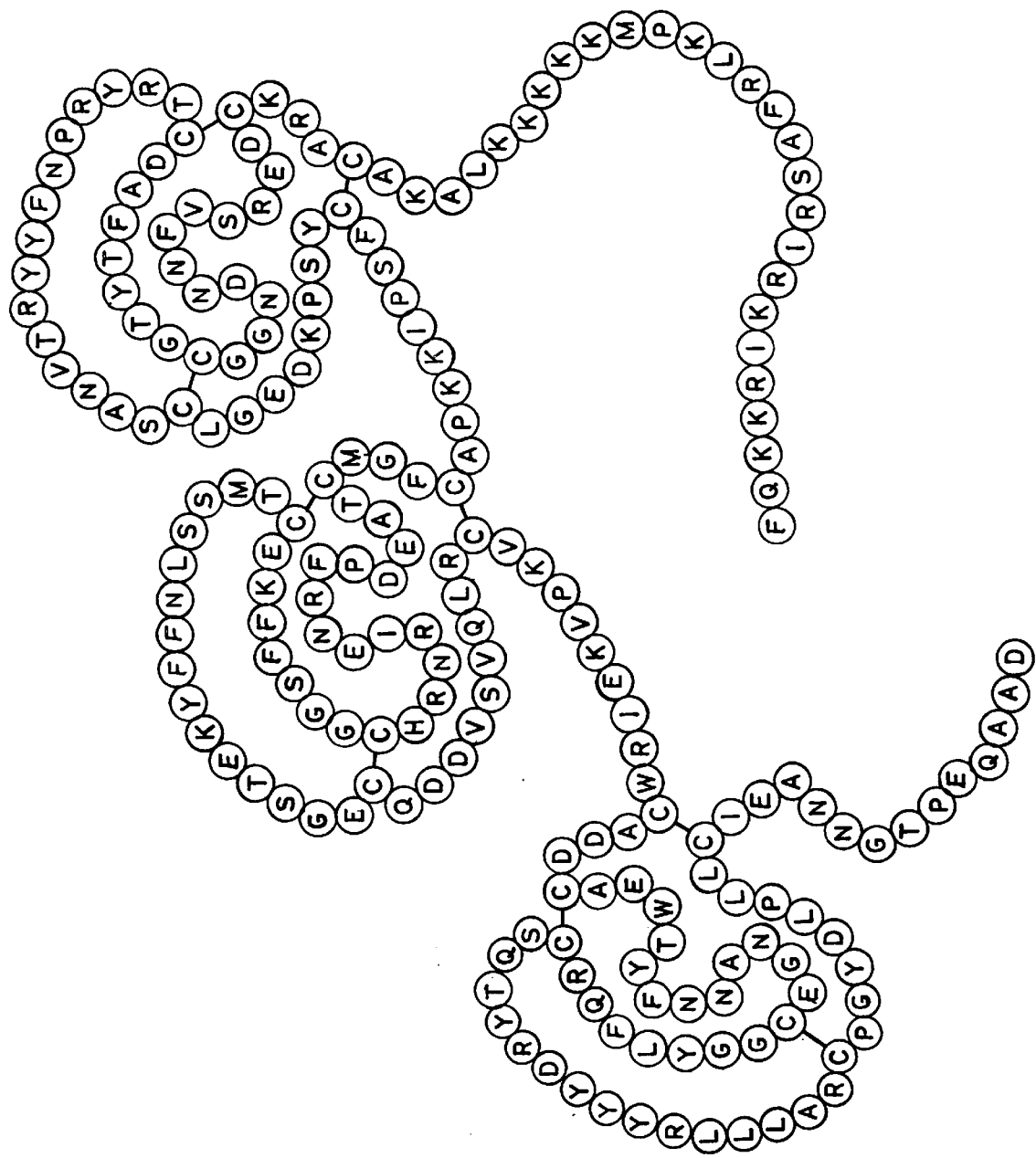

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 276 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
      (A) ORGANISM: Homo sapiens (ix) FEATURE:
      (A) NAME/KEY: Active-site
      (B) LOCATION: 2..3
      (D) OTHER INFORMATION: /note= "Site of partial
          phosphorylation"

(ix) FEATURE:
      (A) NAME/KEY: Active-site
      (B) LOCATION: 117..118
      (D) OTHER INFORMATION: /note= "Potential site for N-linked
          glycosylation"

(ix) FEATURE:
      (A) NAME/KEY: Active-site
      (B) LOCATION: 167..168
      (D) OTHER INFORMATION: /note= "Potential site for N-linked
          glycosylation"

(ix) FEATURE:
      (A) NAME/KEY: Active-site
      (B) LOCATION: 228..229
      (D) OTHER INFORMATION: /note= "Potential site for N-linked
          glycosylation"

(ix) FEATURE:
      (A) NAME/KEY: Domain
      (B) LOCATION: 26..76
      (D) OTHER INFORMATION: /label= Kunitz-1

(ix) FEATURE:
      (A) NAME/KEY: Domain
      (B) LOCATION: 97..147
      (D) OTHER INFORMATION: /label= Kunitz-2

(ix) FEATURE:
      (A) NAME/KEY: Domain
      (B) LOCATION: 189..239
      (D) OTHER INFORMATION: /label= Kunitz-3

(xi) SEQUENCE DESCRIPTION: SEQ ID NO:1:

Asp Ser Glu Glu Asp Glu Glu His Thr Ile Ile Thr Asp Thr Glu Leu
  1               5                   10                  15

Pro Pro Leu Lys Leu Met His Ser Phe Cys Ala Phe Lys Ala Asp Asp
                  20                  25                  30

Gly Pro Cys Lys Ala Ile Met Lys Arg Phe Phe Phe Asn Ile Phe Thr
                  35                  40                  45

Arg Gln Cys Glu Glu Phe Ile Tyr Gly Gly Cys Glu Gly Asn Gln Asn
          50                  55                  60

```
Arg Phe Glu Ser Leu Glu Glu Cys Lys Lys Met Cys Thr Arg Asp Asn
 65                  70                  75                  80

Ala Asn Arg Ile Ile Lys Thr Thr Leu Gln Gln Glu Lys Pro Asp Phe
                 85                  90                  95

Cys Phe Leu Glu Glu Asp Pro Gly Ile Cys Arg Gly Tyr Ile Thr Arg
                100                 105                 110

Tyr Phe Tyr Asn Asn Gln Thr Lys Gln Cys Glu Arg Phe Lys Tyr Gly
                115                 120                 125

Gly Cys Leu Gly Asn Met Asn Asn Phe Glu Thr Leu Glu Glu Cys Lys
        130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
                180                 185                 190

Ala Asp Arg Gly Leu Cys Arg Ala Asn Glu Asn Arg Phe Tyr Tyr Asn
                195                 200                 205

Ser Val Ile Gly Lys Cys Arg Pro Phe Lys Tyr Ser Gly Cys Gly Gly
        210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
                260                 265                 270

Val Lys Asn Met
            275

(2) INFORMATION FOR SEQ ID NO:2:

(i) SEQUENCE CHARACTERISTICS:
        (A) LENGTH: 213 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Homo sapiens (xi) SEQUENCE DESCRIPTION: SEQ ID NO:2:

Asp Ala Ala Gln Glu Pro Thr Gly Asn Asn Ala Glu Ile Cys Leu Leu
 1               5                  10                  15

Pro Leu Asp Tyr Gly Pro Cys Arg Ala Leu Leu Leu Arg Tyr Tyr Tyr
                20                  25                  30

Asp Arg Tyr Thr Gln Ser Cys Arg Gln Phe Leu Tyr Gly Gly Cys Glu
            35                  40                  45

Gly Asn Ala Asn Asn Phe Tyr Thr Trp Glu Ala Cys Asp Asp Ala Cys
        50                  55                  60

Trp Arg Ile Glu Lys Val Pro Lys Val Cys Arg Leu Gln Val Ser Val
 65                  70                  75                  80

Asp Asp Gln Cys Glu Gly Ser Thr Glu Lys Tyr Phe Phe Asn Leu Ser
```

-continued

```
                        85                      90                       95
        Ser Met Thr Cys Glu Lys Phe Phe Ser Gly Gly Cys His Arg Asn Arg
                    100                     105             110

Ile Glu Asn Arg Phe Pro Asp Glu Ala Thr Cys Met Gly Phe Cys Ala
                115                     120                 125

Pro Lys Lys Ile Pro Ser Phe Cys Tyr Ser Pro Lys Asp Glu Gly Leu
            130                 135                 140

Cys Ser Ala Asn Val Thr Arg Tyr Tyr Phe Asn Pro Arg Tyr Arg Thr
        145                 150                 155                 160

Cys Asp Ala Phe Thr Tyr Thr Gly Cys Gly Gly Asn Asp Asn Asn Phe
                        165                 170                 175

Val Ser Arg Glu Asp Cys Lys Arg Ala Cys Ala Lys Ala Leu Lys Lys
                    180                 185             190

Lys Lys Lys Met Pro Lys Leu Arg Phe Ala Ser Arg Ile Arg Lys Ile
                195             200                 205

Arg Lys Lys Gln Phe
            210
```

COMPOSITIONS AND METHODS FOR INHIBITING CELLULAR PROLIFERATION

FIELD OF THE INVENTION

The present invention relates to compositions and methods for the inhibition of cellular proliferation. More particularly, the present invention relates to the use of tissue factor pathway inhibitor and inhibitory fragments thereof to inhibit angiogenesis and angiogenesis-related diseases.

BACKGROUND OF THE INVENTION

Cellular proliferation is a normal ongoing process in all living organisms and is one that involves numerous factors and signals that are delicately balanced to maintain regular cellular cycles. The general process of cell division is one that consists of two sequential processes: nuclear division (mitosis), and cytoplasmic division (cytokinesis). Because organisms are continually growing and replacing cells, cellular proliferation is a central process that is vital to the normal functioning of almost all biological processes. Whether or not mammalian cells will grow and divide is determined by a variety of feedback control mechanisms, which include the availability of space in which a cell can grow and the secretion of specific stimulatory and inhibitory factors in the immediate environment.

When normal cellular proliferation is disturbed or somehow disrupted, the results can be inconsequential or they can be the manifestation of an array of biological disorders. Disruption of proliferation could be due to a myriad of factors such as the absence or overabundance of various signaling chemicals or presence of altered environments. Some disorders characterized by abnormal cellular proliferation include cancer, abnormal development of embryos, improper formation of the corpus luteum, difficulty in wound healing as well as malfunctioning of inflammatory and immune responses.

Cancer is characterized by abnormal cellular proliferation. Cancer cells exhibit a number of properties that make them dangerous to the host, often including an ability to invade other tissues and to induce capillary ingrowth, which assures that the proliferating cancer cells have an adequate supply of blood. One of the defining features of cancer cells is that they respond abnormally to control mechanisms that regulate the division of normal cells and continue to divide in a relatively uncontrolled fashion until they kill the host.

Angiogenesis and angiogenesis related diseases are closely affected by cellular proliferation. As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" is defined herein as a thin layer of flat cells that lines serous cavities, lymph vessels, and blood vessels. These cells are defined herein as "endothelial cells". The term "endothelial inhibiting activity" means the capability of a molecule to inhibit angiogenesis in general. The inhibition of endothelial cell proliferation also results in an inhibition of angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic-dependent, angiogenic-associated, or angiogenic-related diseases. These diseases are therefore a result of abnormal or undesirable cell proliferation, particularly endothelial cell proliferation.

The hypothesis that tumor growth is angiogenesis-dependent was first proposed in 1971 by Judah Folkman (*N. Engl. Jour. Med.* 285:1182 1186, 1971) In its simplest terms the hypothesis proposes that once tumor "take" has occurred, every increase in tumor cell population must be preceded by an increase in new capillaries converging on the tumor. Tumor "take" is currently understood to indicate a prevascular phase of tumor growth in which a population of tumor cells occupying a few cubic millimeters volume and not exceeding a few million cells, survives on existing host microvessels. Expansion of tumor volume beyond this phase requires the induction of new capillary blood vessels. For example, pulmonary micrometastases in the early prevascular phase in mice would be undetectable except by high power microscopy on histological sections.

Further indirect evidence supporting the concept that tumor growth is angiogenesis dependent is found in U.S. patent application Ser. No. 08/429,743 now U.S. Pat. No. 5,885,735 which is incorporated herein by reference.

Thus, it is clear that cellular proliferation, particularly endothelial cell proliferation, and most particularly angiogenesis, plays a major role in the metastasis of a cancer. If this abnormal or undesirable proliferation activity could be repressed, inhibited, or eliminated, then the tumor, although present, would not grow. In the disease state, prevention of abnormal or undesirable cellular proliferation and angiogenesis could avert the damage caused by the invasion of the new microvascular system. Therapies directed at control of the cellular proliferative processes could lead to the abrogation or mitigation of these diseases.

What is needed therefore is a composition and method which can inhibit abnormal or undesirable cellular proliferation, especially the growth of blood vessels into tumors. The composition should be able to overcome the activity of endogenous growth factors in premetastatic tumors and prevent the formation of the capillaries in the tumors thereby inhibiting the development of disease and the growth of tumors. The composition should also be able to modulate the formation of capillaries in angiogenic processes, such as wound healing and reproduction. Finally, the composition and method for inhibiting cellular proliferation should preferably be non-toxic and produce few side effects.

SUMMARY OF THE INVENTION

In accordance with the present invention, compositions and methods are provided that are effective in inhibiting abnormal or undesirable cell proliferation, especially endothelial cell proliferation and angiogenesis related to tumor growth. The composition provided herein contains a protein known as "tissue factor pathway inhibitor" (TFPI), a TFPI homolog, or an active fragment thereof, wherein the fragment is defined by its ability to exhibit antiproliferative activity on human and other animal endothelial cells. Tissue factor pathway inhibitor is a protein having a molecular weight of between approximately 32 kilodaltons and 45 kilodaltons and having a structure of approximately 276 amino acids consisting of an acidic amino terminus followed by three Kunitz-type protease inhibitor domains and a basic carboxyl terminal region.

The methods provided herein for treating diseases and processes mediated by undesired and uncontrolled cell proliferation, such as cancer, involve administering to a human or animal a composition containing a substantially purified tissue factor pathway inhibitor (TFPI), TFPI homolog, or active fragment thereof, in a dosage sufficient to inhibit cell proliferation, particularly endothelial cell proliferation. The method is especially useful for treating or repressing the growth of tumors, particularly by inhibiting angiogenesis. Administration of the composition to a human or animal having prevascularized metastasized tumors is useful for preventing the growth or expansion of those tumors.

Accordingly, it is an object of the present invention to provide a method of treating diseases and processes that are mediated by abnormal or undesirable cellular proliferation.

It is another object of the present invention to provide a composition for treating or repressing the growth of a cancer.

It is yet another object of the present invention to provide a therapy for cancer that has minimal side effects.

It is another object of the present invention to provide a method and composition for treating diseases and processes that are mediated by angiogenesis.

These and other objects, features and advantages of the present invention will become apparent after a review of the following detailed description of the disclosed embodiments and the appended claims.

BRIEF DESCRIPTION OF THE FIGURES

FIG. 1 is a schematic diagram of tissue factor pathway inhibitor (TFPI) showing its structure, including the three Kunitz domains.

FIG. 2 is a diagram of the blood coagulation cascade.

FIGS. 3a–3d are graphs depicting the results of proliferation assays testing various forms of TFPI using uridine incorporation: FIG. 3a is a graph showing the antiproliferative activity of full length TFPI purified from human plasma. FIG. 3b is a graph showing the antiproliferative activity of TFPI purified from HepG2 cells. FIG. 3c is a graph showing the antiproliferative activity of full length recombinant TFPI. FIG. 3d is a graph showing the antiproliferative activity of recombinant TFPI using cell counting.

FIGS. 5a and 5b are graphs showing cell proliferation activity after administration of TFPI and Heparin. In FIG. 5a, equimolar concentrations of TFPI and heparin were used. In FIG. 5b, the concentration of heparin was 5-fold in excess of the concentration of TFPI.

FIG. 7 is a schematic diagram of tissue factor pathway inhibitor-2 (TFPI-2) showing its structure, including the three Kunitz domains.

DETAILED DESCRIPTION

Figure 3A:
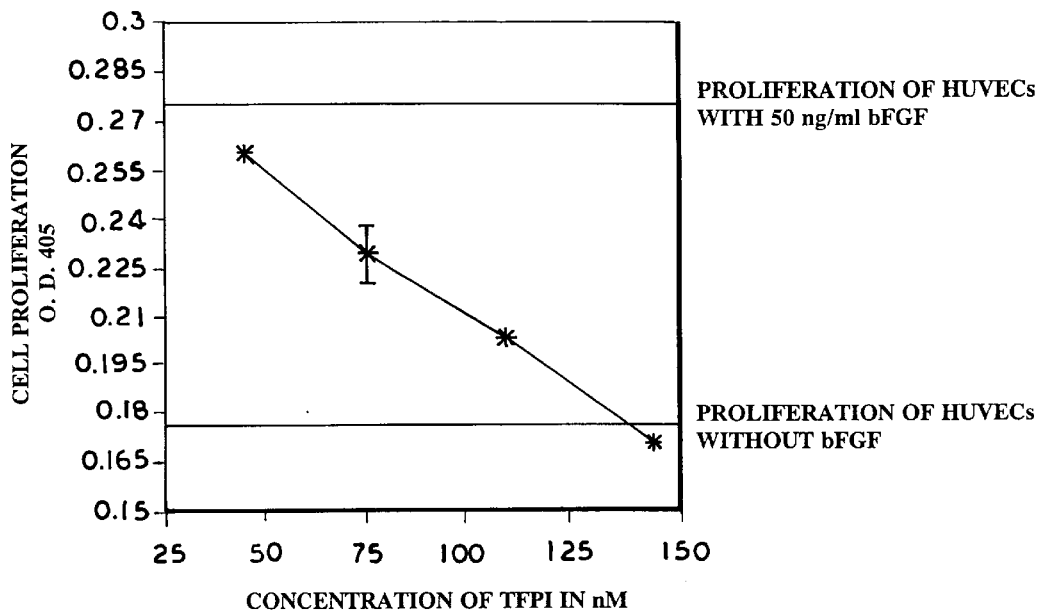
Figure 3B:
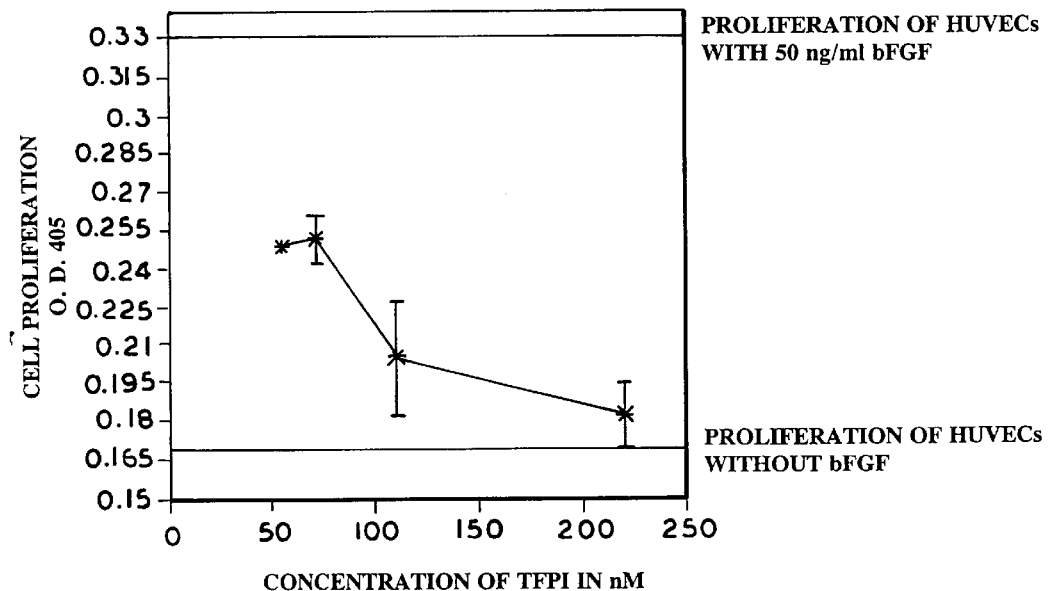

Compositions and methods for the treatment of diseases and processes that are mediated by or associated with abnormal or undesirable cellular proliferation are provided. The composition contains tissue factor pathway inhibitor (TFPI). TFPI is defined herein as including TFPI homologs such as TFPI-2. TFPI is also defined herein as including active fragments of the tissue factor pathway inhibitor molecule. Active fragments of TFPI are defined herein as fragments having the ability to exhibit anti-proliferative activity on human and other animal endothelial cells by in vivo or in vitro assays or other known techniques. Active fragments of TFPI are further defined herein as fragments having an inhibitory or repressive effect on angiogenesis. TFPI is further defined as including proteins or active fragments thereof belonging to a family, or superfamily, of proteins that contain Kunitz-type protease inhibitor (KPI) domains, such as amyloid beta precursor protein and other serine protease inhibitors.

In accordance with the method, TFPI is administered to a human or animal exhibiting undesirable cell proliferation in an amount sufficient to inhibit the undesirable cell proliferation, particularly endothelial cell proliferation, angiogenesis or an angiogenesis-related disease.

TFPI Characteristics

TFPI, as defined herein, is a glycoprotein having a molecular weight of approximately 32 to 45 kilodaltons. TFPI is composed of approximately 276 amino acids organized in a structure that includes an acidic amino terminus followed by three Kunitz-type protease inhibitor domains, referred to as Kunitz-1, Kunitz-2, and Kunitz-3, and a basic carboxyl terminal region as shown in FIG. 1. TFPI has a total of three glycosylation sites, located at amino acids 117, 167, and 228.

TFPI, also known to those skilled in the art as lipoprotein-associated coagulation inhibitor, is a protease inhibitor that plays an important role in the regulation of tissue factor-induced blood coagulation. TFPI functions primarily by interfering with the function of certain components in the blood coagulation system, more specifically by binding and inactivating factor X and binding to and inhibiting Tissue Factor/VIIa.

Blood coagulation is complex series of interactions and is usually described as a cascade type reaction wherein a sequence of reactions involves numerous enzymes and cofactors. Coagulation consists of both an intrinsic and extrinsic pathway, the end result of which is the conversion of fibrinogen to fibrin. The blood coagulation cascade is shown in FIG. 2.

The extrinsic system occurs in parallel with the intrinsic system and may be defined as coagulation initiated by components present entirely within the vascular system. Trauma to endothelial cells causes the conversion of Factor VII to Factor VII$_a$ which, in the presence of Tissue Factor (TF), activates Factor X converting it to Factor X$_a$. Once Factor X$_a$ is formed it converts prothrombin to thrombin, which finally facilitates the conversion of fibrinogen to fibrin in the presence of thrombin, and from fibrin to a cross-linked fibrin clot.

In the blood coagulation cascade, TFPI blocks the initial steps of the extrinsic pathway by binding and inactivating factor Xa and by binding and inhibiting tissue factor/factor VIIa complex. The Kunitz-1 domain of TFPI is responsible for the inhibition of factor VIIa of the tissue factor/factor VIIa complex while the Kunitz-2 domain is responsible for the inhibition of factor Xa. The role of Kunitz-3 is not yet understood, although a heparin-binding site has been localized in its basic region. The main heparin-binding site of TFPI is located in the carboxyl terminus of the molecule.

TFPI Localization and Production

Generally, TFPI is found in plasma, in platelets and on endothelium. Its plasma concentration is low (approximately 3 nM), and the majority of circulating TFPI is bound to lipoproteins (LDL, HDL, and lipoprotein (a)). Platelets carry approximately 10% of the total TFPI concentration, and they release it after acute stimulation. At a site of blood vessel injury and after the bleeding has stopped, there is a three-fold increase in the concentration of TFPI compared to the normal levels found in plasma. This additional TFPI is derived by the aggregated platelets at the site of the injury. The majority of intravascular TFPI is endothelium-bound and is released after heparin infusion. The amount of the heparin-releasable TFPI is believed to be two to ten times the amount found in plasma or 220–800 ng/ml.

Intravascular TFPI exists in several forms. The predominant forms of plasma TFPI have molecular weights of 34 and 41 KDa but other forms with higher molecular weights are also present. The form of TFPI that circulates while bound to LDL has a molecular mass of 34 KDa and lacks the carboxyl-terminal region and part of the Kunitz-3 domain. The 41 KDa form of TFPI circulates while bound to HDL and is truncated like one of the 34 KDa forms. This form of TFPI has a higher molecular weight because it is linked via a disulfide bond to apolipoprotein A-II. The heparin-releasable TFPI is not truncated and is fully glycosylated.

TFPI is synthesized in endothelial cells and is exocytosed toward the surface of the cells where it remains bound to heparin sulfate proteoglycans (HSPGs). The liver is mainly responsible for the clearance of circulating TFPI. In the liver, the low density lipoprotein receptor-related protein (LRP) mediates the uptake and degradation of TFPI by hepatoma cells. This LRP-mediated clearance of TFPI involves two steps. Initially TFPI binds to HSPGs on the surface of the cells and is then transferred to LRP for internalization.

TFPI is isolated from body fluids including, but not limited to, serum, urine, and ascites, or synthesized by chemical or biological methods, such as cell culture, recombinant gene expression, and peptide synthesis. Recombinant techniques include gene amplification from DNA sources using the polymerase chain reaction (PCR), and gene amplification from RNA sources using reverse transcriptase/PCR. The amino acid sequence of TFPI is known and is set forth schematically in FIG. 1 and in SEQ ID No. 1. By definition, fragments of TFPI have an amino acid sequence within the amino acid sequence set forth in SEQ ID No. 1. TFPI is extracted from body fluids by known protein extraction methods, particularly the method described by Novotny, W. F., et al., "Purification and Characterization of the Lipoprotein-Associated Coagulation Inhibitor From Human Plasma", *J. Biol. Chem.* 1989; 264; 18832–18837.

TFPI-2 is a homolog of TFPI and has a molecular mass of 32 kDa. The amino acid sequence of TFPI is known and is set forth schematically in FIG. 7 and in SEQ ID No. 2. By definition, fragments of TFPI-2 have an amino acid sequence within the amino acid sequence set forth in SEQ ID No. 2. Characteristics of TFPI-2 are described in the scientific article of Sprecher, Cindy A., et al., *Proc. Natl. Acad. Sci., USA,* 91:3353–3357 (1994), which is incorporated by reference herein. TFPI-2 is also known by those skilled in the art as placental protein 5 as described in the scientific article of Miyagi, Y., et al., *J. Biochem.* 116:939–942 (1994), which is incorporated by reference herein. Additional properties of TFPI-2 are described in the scientific article of Petersen, L. C., et al., *Biochem.* 35:266–272 (1996), which is incorporated by reference herein.

TFPI Fragments

TFPI fragments can be produced and tested for antiproliferative activity using techniques and methods known to those skilled in the art. For example, full length recombinant TFPI (rTFPI) can be produced using the Baculovirus system. The full length TFPI can be cleaved into individual domains or digested using various methods such as, for example, the method described by Enjyoji et al. (*Biochemistry* 34:5725–5735 (1995)). In accordance with the method of Enjyoji et al., rTFPI is treated with human neutrophil elastase, and the digest purified using a heparin column. Human neutrophil elastase cleaves TFPI at Leu$^{89}$ into two fragments: one containing Kunitz-1 and the other containing Kunitz-2 and Kunitz-3. The fragment containing Kunitz-2 and Kunitz-3 (Kunitz-2/Kunitz-3) is further treated with hydroxylamine according to the method of Balian et al. (*Biochemistry* 11:3798–3806 (1972)), and the digest purified using a heparin column. Hydroxylamine cleaves the fragment containing Kunitz-2 and Kunitz-3 into two fragments: one containing Kunitz-3 and the other containing the Kunitz-2 domain. The fragments containing the Kunitz-1 domain, Kunitz-2 domain, Kunitz-3 domain, and Kunitz-2/Kunitz-3 domain are then tested for the ability to inhibit bFGF-induced cell proliferation, particularly endothelial cell proliferation as described in the Examples below. As described in the Examples, fragments containing the Kunitz-3 domain have been shown to have anti-proliferative activity.

Alternatively, fragments are prepared by digesting the entire TFPI molecule, or large fragments thereof exhibiting anti-proliferative activity, to remove one amino acid at a time. Each progressively shorter fragment is then tested for anti-proliferative activity. Similarly, TFPI fragments of various lengths may be synthesized and tested for anti-proliferative activity. By increasing or decreasing the length of a fragment, one skilled in the art may determine the exact number, identity, and sequence of amino acids within the TFPI molecule that are required for anti-proliferative activity using routine digestion, synthesis, and screening procedures known to those skilled in the art.

Anti-proliferative activity is evaluated in situ by testing the ability of TFPI fragments to inhibit the proliferation of new blood vessel cells, referred to herein as the inhibition of angiogenesis. A suitable assay is the chick embryo chorio-allantoic membrane (CAM) assay described by Crum et al., *Science* 230:1375 (1985) and described in U.S. Pat. No. 5,001,116, which is incorporated by reference herein. The CAM assay is briefly described as follows. Fertilized chick embryos are removed from their shell on day 3 or 4, and a methylcellulose disc containing the TFPI fragment composition is implanted on the chorioallantoic membrane. The embryos are examined 48 hours later and, if a clear avascular zone appears around the methylcellulose disc, the diameter of that zone is measured. The larger the diameter of the zone, the greater the anti-angiogenic activity.

TFPI Compositions

A composition containing TFPI, a TFPI homolog, or an active fragment of TFPI or a TFPI homolog, can be prepared in a physiologically acceptable formulation, such as in a pharmaceutically acceptable carrier, using known techniques. For example, TFPI, a TFPI homolog, or an active fragment thereof is combined with a pharmaceutically acceptable excipient to form a therapeutic composition.

Alternatively, the gene for TFPI or peptide fragments thereof may be delivered in a vector for continuous TFPI administration using gene therapy techniques. The vector may be administered in a vehicle having specificity for a target site, such as a tumor.

The therapeutic composition may be in the form of a solid, liquid or aerosol. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic angiogenesis-modulating composition, for example, subcutaneously. Examples of liquid compositions include formulations adapted for injection subcutaneously, intravenously, intra-arterially, and formulations for topical and intraocular administration. Examples of aerosol formulations include inhaler formulations for administration to the lungs.

The composition may be administered by standard routes of administration. In general, the composition may be administered by topical, oral, rectal, nasal or parenteral (for example, intravenous, subcutaneous, or intermuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either of polylactide, polyglycolide, or polylactide co-glycolide (co-polymers of lactic acid and glycolic acid).

The dosage of the composition will depend on the condition being treated, the particular composition used, and other clinical factors such as weight and condition of the patient, and the route of administration.

The composition may be administered in combination with other compositions and procedures for the treatment of diseases. For example, unwanted cell proliferation may be treated conventionally with surgery, radiation or chemotherapy in combination with the administration of TFPI, TFPI homologs, or active fragments thereof, and additional doses of TFPI, TFPI homologs, or active fragments thereof may be subsequently administered to the patient to stabilize and inhibit the growth of any residual unwanted cell proliferation.

The methods and compositions are useful for treating diseases and processes that are mediated by abnormal or undesirable cellular proliferation, particularly abnormal or undesirable endothelial cell proliferation, including, but not limited to, hemangioma, solid tumors, leukemia, metastasis, telangiectasia psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation. The method and composition are particularly useful for treating angiogenesis-related disorders and diseases by inhibiting angiogenesis. As described in more detail below, recombinant, full length TFPI is approximately ten times more potent for inhibiting angiogenesis than other known endogenous inhibitors of angiogenesis such as recombinant PF-4, and Kringle 1–3 of the Angiostatin™ molecule.

The methods and compositions described herein are particularly useful for treating cancer, arthritis, macular degeneration, and diabetic retinopathy This invention is further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Effect of TFPI on bFGF-induced Proliferation of Human Endothelial Cells

Proliferation assays familiar to those skilled in the art using human umbilical vein endothelial (HUVE) cells were used to determine the effect of TFPI on bFGF-induced proliferation of human umbilical vein endothelial cells.

TFPI from the following sources was tested:
1. full length, fully glycosylated TFPI (molecular weight 43,000) purified from human plasma
2. TFPI purified from HepG2 cells containing full length and carboxyl-terminal lacking molecules
3. full length, partially glycosylated TFPI (molecular weight 35,000) produced recombinantly
4. truncated, partially glycosylated (molecular weight 21,000) produced recombinantly Materials and Methods The materials for this experiment included HUVE cells and media for their proliferation, Endothelial Cell Basal Medium (EBM) and Endothelial Cell Growth Medium (EGM), (Clonetics, San Diego, Calif.). Also used was TFPI purified from human plasma or HepG2 cells, recombinant full length TFPI, and recombinant truncated TFPI (1–160 amino acids) (all from American Diagnostica Inc., Greenwich, Conn.). In addition, a cell proliferation ELISA BrdU (Boehringer Mannheim Corporation, Indianapolis, Ind.), bFGF (R&D, Minneapolis, Minn.) and heparin (Sigma Chemical Company, St. Louis, Mo.) were used.

The proliferation assay involved the routine culturing of human umbilical vein endothelial (HUVE) cells to confluency in EGM media. The cells were trypsinized and plated in a 96-well plate at 5000 cells per well per 100 $\mu$L EBM media. The cells were allowed to adhere to the plate for at least 2 hours. Next, bFGF at 10 ng/ml and TFPI at various concentrations were added to the wells. The cells were cultured for 48 hours after which cell proliferation was determined using a standard uridine incorporation method.

Results

Figure 4:
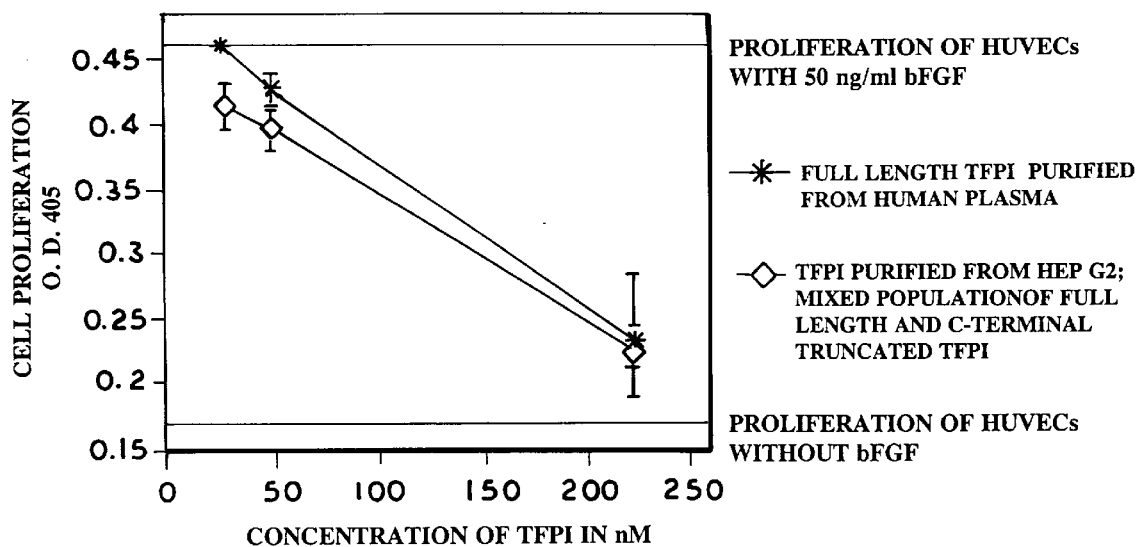
FIG. 4 is a graph comparing the antiproliferative activity of TFPI purified from human plasma and TFPI purified HepG2 cells in a HUVE cell proliferation assay.

As indicated below, TFPI from all three sources inhibited bFGF-induced proliferation of human umbilical vein endothelial cells. The relative proliferative effects of TFPI are shown graphically in FIGS. 3a–3d. TFPI purified from human plasma and HepG2 cells had comparable activities indicating that neither glycosylation nor heparin binding was responsible for the antiproliferative activity of TFPI. (FIG. 4).

| Source of TFPI | Effect on Proliferation |
| --- | --- |
| Purified From Human Plasma | Inhibition of Proliferation |
| Purified From HepG2 cells | Inhibition of Proliferation |
| Recombinant, Full Length (1–216 amino acids) | Inhibition of Proliferation |
| Recombinant, truncated (1–160 amino acids) | No Inhibition of Proliferation |

EXAMPLE 2

Effect of Heparin on TFPI Inhibition of bFGF-induced Proliferation

Proliferation assays using HUVE cells, as described in Example 1, were used to determine the effect of heparin on TFPI inhibition of bFGF-induced proliferation. The purpose of this study was to determine whether heparin was able to neutralize the antiproliferative activity of TFPI.

TFPI was pre-incubated with equimolar concentrations of heparin and with concentrations of heparin that were five-fold in excess of the concentration of TFPI. The results are summarized below and are presented graphically in FIGS. 5a and 5b.

| Relative Concentration of Heparin & TFPI | Antiproliferative Activity of TFPI |
| --- | --- |
| Equimolar Heparin and TFPI | No Effect |
| Heparin 5-fold excess > TFPI | No Effect |

When TFPI was pre-incubated with equimolar and five-fold in excess concentrations of heparin, it did not lose its antiproliferative activity. Together these data demonstrate that TFPI does not inhibit bFGF induced proliferation of endothelial cells by binding to HSPGs on the surface of the cells and thus obstructing the binding of bFGF to heparin sulfates.

EXAMPLE 3

Comparison of the Effects of Native and Recombinant TFPI on bFGF-induced Proliferation of Endothelial Cells Cell proliferation assays, as described in Example 1, were conducted to determine the relative potency of native TFPI versus recombinant TFPI.

Results

Fifty percent inhibition of the bFGF-induced proliferation of HUVE cells was obtained with 75 nM for the full length, fully glycosylated native TFPI and with 150 nM for the full length, recombinant TFPI. Therefore, there is a significant difference in the ability to inhibit proliferation by native and recombinant TFPI, with native TFPI being decidedly more potent.

EXAMPLE 4

Comparison of the Inhibitory Activity of Recombinant TFPI to Other Endogenous Angiogenesis Inhibitors Cell proliferation assays, as described in Example 1, were conducted using full length recombinant TFPI, Platelet Factor 4 (PF-4), and recombinant Kringle 1–3 of Angiostatin™ peptide. Both PF-4 and Angiostatin™ peptide are known endogenous inhibitors of angiogenesis. PF-4 is a protein involved in the blood coagulation cascade and is referenced as an inhibitor of angiogenesis by Maione, T. et al. in the article "Inhibition of Angiogenesis by Recombinant Human Platelet Factor-4 and Related Peptides" *Science* 247:77 (1990). Angiostatin is a fragment of plasminogen and its inhibitory effect on angiogenesis is described by Cao, Y. et al. in the article "Kringle Domains of Human Angiostatin" *J. Biol. Chem.* 271:1 (1996).

PF-4 and TFPI were tested for inhibition of human umbilical vein endothelial cell (HUVEC) proliferation. Angiostatin™ peptide was tested for the inhibition of bovine capillary endothelial (BCE) proliferation. The results are summarized below.

Results

| Angiogenesis Inhibitor | Concentration for 50% Inhibition |
| --- | --- |
| Recombinant TFPI | Approx. 0.125 µm |
| PF-4 | 1.25 µm |
| Kringle 1-3 Angiostatin ™ | 0.190 µm |

Full length recombinant TFPI is approximately ten times more potent than recombinant PF-4, which requires 1.25 µM for 50% inhibition of HUVE cell proliferation. Full length recombinant TFPI is also more active than recombinant Kringle 1–3 of angiostatin, which requires approximately 0.190 µM for 50% inhibition of BCE proliferation.

EXAMPLE 5

Localization of Relevant Domains of Recombinant TFPI for Inhibitory Activity on Proliferation of Endothelial Cells Cell proliferation assays, as described above in Example 1, were conducted using fragments of recombinant TFPI containing the following domains: Kunitz-1, Kunitz-2, or Kunitz-3.

Results

Figure 6:
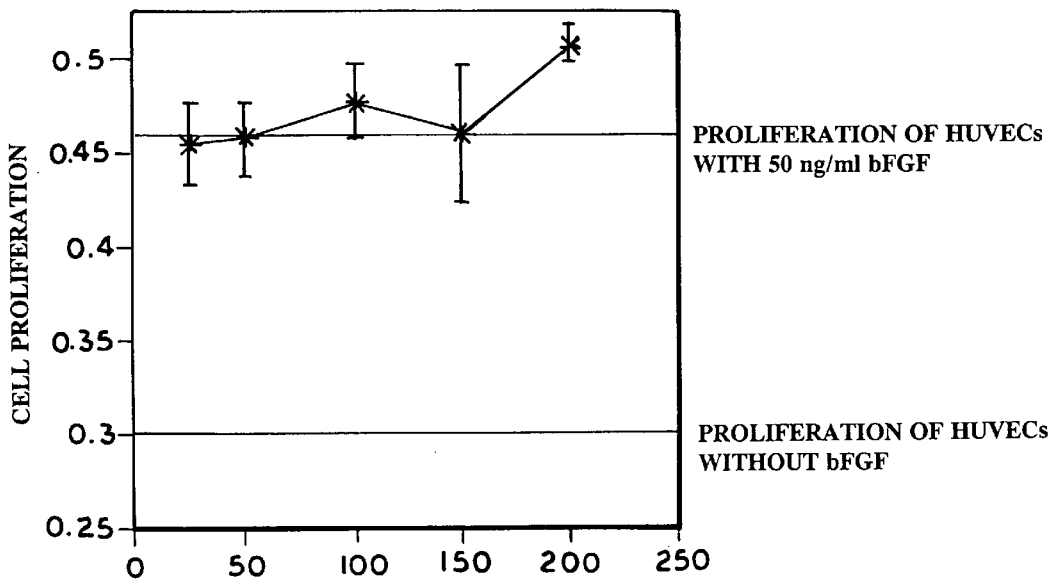
FIG. 6 is a graph depicting the effect of recombinant TFPI containing only the first two Kunitz domains on proliferation of HUVE cells.

Recombinant TFPI containing only Kunitz-1, and Kunitz-2 (1–160 amino acids) did not result in the inhibition of proliferation of endothelial cells. However, recombinant TFPI containing Kunitz-3 did result in the inhibition of proliferation as shown in FIG. 6. These results indicate that Kunitz-3 or an active portion thereof most probably plays an important role affecting the activity of TFPI or the binding of TFPI to its receptor on the surface of the endothelial cells.

We claim:

1. A method of inhibiting endothelial cell proliferation in a human or animal comprising,
administering to the human or animal a sufficient amount of a composition comprising tissue factor pathway inhibitor to inhibit endothelial cell proliferation, wherein the tissue factor pathway inhibitor has an amino acid sequence comprising the amino acid sequence set forth in SEQ ID NO: 1. or anti-proliferative fragments thereof.

2. The method of claim 1 wherein the endothelial cell proliferation occurs during angiogenesis-related disease.

3. The method of claim 2, wherein the angiogenesis-related disease is a disease selected from the group consisting of cancer, arthritis, macular degeneration, and diabetic retinopathy.

4. The method of claim 1 wherein administration of the composition inhibits angiogenesis.

5. A method of inhibiting endothelial cell proliferation in a human or animal comprising,
administering to the human or animal a sufficient amount of a composition comprising tissue factor pathway inhibitor to inhibit endothelial cell proliferation, wherein the tissue factor pathway inhibitor has an amino acid sequence comprising the amino acid sequence set forth in SEQ ID NO: 2. or anti-proliferative fragments thereof.

6. The method of claim 5 wherein the anti-proliferative fragment contains the Kunitz-3 domain or an anti-proliferative fragment thereof.

7. The method of claim 5 wherein the anti-proliferative fragment contains the Kunitz-3 domain or an anti-proliferative fragment thereof.

8. The method of claim 1 wherein the composition comprises the tissue factor pathway inhibitor and a pharmaceutically acceptable excipient, carrier or sustained-release matrix.

9. The method of claim 1 wherein the inhibition of endothelial cell proliferation inhibits neovascularization.

* * * * *